United States Patent
Goto (10) Patent No.: US 10,905,467 B2
(45) Date of Patent: Feb. 2, 2021

(54) METHOD FOR LIFTING MUCOSA (71) Applicant: OLYMPUS CORPORATION, Hachioji (JP)

(72) Inventor: Osamu Goto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 219 days.

(21) Appl. No.: 15/928,401

(22) Filed: Mar. 22, 2018

(65) Prior Publication Data

US 2019/0290325 A1    Sep. 26, 2019

(51) Int. Cl.
*A61B 17/02*     (2006.01)
*A61B 17/00*     (2006.01)
*A61B 17/34*     (2006.01)

(52) U.S. Cl.
CPC .... *A61B 17/3478* (2013.01); *A61B 17/00234* (2013.01); *A61B 17/0281* (2013.01); *A61B 2017/00269* (2013.01)

(58) Field of Classification Search
CPC ................. A61B 17/0281; A61B 2017/00269
See application file for complete search history.

(56) References Cited

U.S. PATENT DOCUMENTS

| | | | |
|---|---|---|---|
| 7,169,104 B2 | 1/2007 | Ueda et al. | |
| 8,038,612 B2 | 10/2011 | Paz | |
| 2006/0111734 A1* | 5/2006 | Kaplan | A61B 17/00234 606/153 |
| 2010/0145352 A1* | 6/2010 | Chang | A61B 17/00234 606/110 |
| 2012/0046525 A1* | 2/2012 | Russell | A61B 17/0218 600/204 |

FOREIGN PATENT DOCUMENTS

| | | |
|---|---|---|
| JP | 2004-344127 A | 12/2004 |
| JP | 2008-155006 A | 7/2008 |
| JP | 2012-510872 A | 5/2012 |
| WO | 2010/065829 A1 | 6/2010 |

OTHER PUBLICATIONS

Reider et al. The suture-pulley method for endolumenal triangulation in endoscopic submucosal dissection. 2011. Endoscopy. 43: pp. E319-E320.*

* cited by examiner

*Primary Examiner* — Martin T Ton
(74) *Attorney, Agent, or Firm* — Oliff PLC (57) ABSTRACT

A method for dissecting a submucosal layer includes: incising at a tissue portion surrounding an area including a lesion in a gastrointestinal tract; fixing a thread first end to the area including the lesion, the suture thread including a second end having a needle, and barbs arranged along a longitudinal axis between the first and second ends; piercing the needle to a tract wall that faces the area including the lesion and pulls the thread through the tract wall into the gastrointestinal tract; holding a state of lifting at least a portion of the area including the lesion by pulling the needle or the thread, lifting a tract wall at least the portion including the lesion, and engaging the barbs with the tract wall; dissecting the submucosal layer of the gastrointestinal tract in the state of lifting at least the portion of the area including the lesion.

10 Claims, 12 Drawing Sheets

METHOD FOR LIFTING MUCOSA

TECHNICAL FIELD

The present invention relates to a method for lifting a mucosa.

BACKGROUND ART

A medical treatment that endoscopically resects a lesion of a gastrointestinal tract is minimally invasive surgery and is capable of performing en bloc resection. This medical treatment has been widely prevalent as a radical treatment. In endoscopic submucosal dissection (ESD), a dissection is performed at a submucosal layer and the lesion is resected after incising the mucosal layer around an area including the lesion. Non-exposed endoscopic wall-inversion surgery (NEWS) is known as one of a procedure which is capable of resecting the area including the lesion without opening an organ lumen of the gastrointestinal tract using an endoscope and a laparoscope. In the procedure of NEWS as with ESD, the mucosa is incised, the dissection is performed at a submucosal layer, and the lesion is resected using the endoscope.

It is necessary for an operation of the submucosal layer to reliably capture the submucosal layer in an imaging view reliably and to proceed during adding an appropriate traction to a dissection part by lifting up the mucosal layer constituting the innermost layer of the gastrointestinal tract accordingly.

However, because an inside of the gastrointestinal tract is an extremely limited space, it is difficult to add the appropriate traction to the dissection part depending on a position of the lesion and a posture of a patient. Therefore, the operation of the submucosal layer is very difficult and the operation takes an amount of time.

In Japanese Unexamined Patent Application, First Publication No. 2008-155006, a mucosa towing tool in which an elastic portion extends and which tows a mucosal layer incised and dissected by attaching a first grasping member to the mucosal layer to be incised and dissected, attaching a second grasping member to another mucosal layer to be incised and dissected, connecting the first grasping member and one end of the elastic portion by the first connecting body, and connecting the second grasping member and the other end of the elastic portion by the second connecting body. The submucosal layer is dissected during towing the mucosal layer of the area including the lesion using the mucosa towing tool disclosed in Japanese Unexamined Patent Application, First Publication No. 2008-155006.

Solution to Problem

According to one aspect of the method for dissecting a submucosal layer, the method includes: an incising step of incising a portion of a tissue surrounding an area including a lesion in a gastrointestinal tract; a fixing step of fixing a first end of a suture thread to the area including the lesion, the suture thread including the first end, a second end to which a needle is connected, and a plurality of barbs that are arranged along a longitudinal axis between the first end and the second end; a piercing step of piercing the needle to a tract wall that faces the area including the lesion and pulls the suture thread passing through the tract wall into the gastrointestinal tract; a lifting step of holding a state of lifting at least a portion of the area including the lesion by pulling the needle or the suture thread that is pulled into the gastrointestinal tract from the tract wall, lifting at least the portion of the area including the lesion, and engaging the plurality of barbs of the suture thread with the tract wall; and a dissecting step of dissecting the submucosal layer of the gastrointestinal tract in the state of lifting at least the portion of the area including the lesion.

According to the above method for dissecting a submucosal layer, the plurality of barbs of the suture thread may include a first barb and a second barb that is arranged closer to the first end side than the first barb; the lifting step may include a first engaging step and a second engaging step; in the first engaging step, the first barb may be engaged with the tract wall by pulling the needle or the suture thread pulled into the gastrointestinal tract from the tract; and in the second engaging step, the second barb may be engaged with the tract wall in a state of further lifting the portion of the area including the lesion T than a position at the time of the first engaging step by pulling the needle or the suture thread pulled into the gastrointestinal tract from the tract after the first engaging step.

According to the above method for dissecting a submucosal layer, in the fixing step, the needle may be passed through the area including the lesion.

According to the above method for dissecting a submucosal layer, in the lifting step, at least the portion of the area including the lesion may be lifted by pulling the needle or the suture thread pulled into the gastrointestinal tract from the tract wall using a grasping instrument; the grasping instrument may be released from the needle or the suture thread after lifting at least the portion of the area including the lesion; and in the dissecting step, the submucosal layer may be dissected in the state of lifting at least the portion of the area including the lesion after releasing the grasping instrument from the needle or the suture thread.

According to the above method for dissecting a submucosal layer, in the lifting step, the amount of lift of at least the portion of the area including the lesion may be increased by increasing the amount of pull of the needle or the suture thread that is pulled into the gastrointestinal tract from the tract wall in accordance with a position at which the submucosal layer is dissected.

According to the above method for dissecting a submucosal layer, in the lifting step, the amount of pull may be varied by adjusting an amount of air supply into the gastrointestinal tract.

According to the above method for dissecting a submucosal layer, the suture thread may be separated into a portion of a thread including the first end of the suture thread that is fixed to the area including the lesion and a remaining thread including the second end of the suture thread that is fixed to the tract wall after dissecting the submucosal layer by cutting the suture thread in a vicinity of the area including the lesion, and a mucosal defect part that is formed by dissecting the submucosal layer may be sutured and closed by suturing using the remaining thread picked from the tract wall.

DESCRIPTION OF EMBODIMENTS

One embodiment of the present invention will be described with reference to FIGS. 1 to 14.

Figure 1:
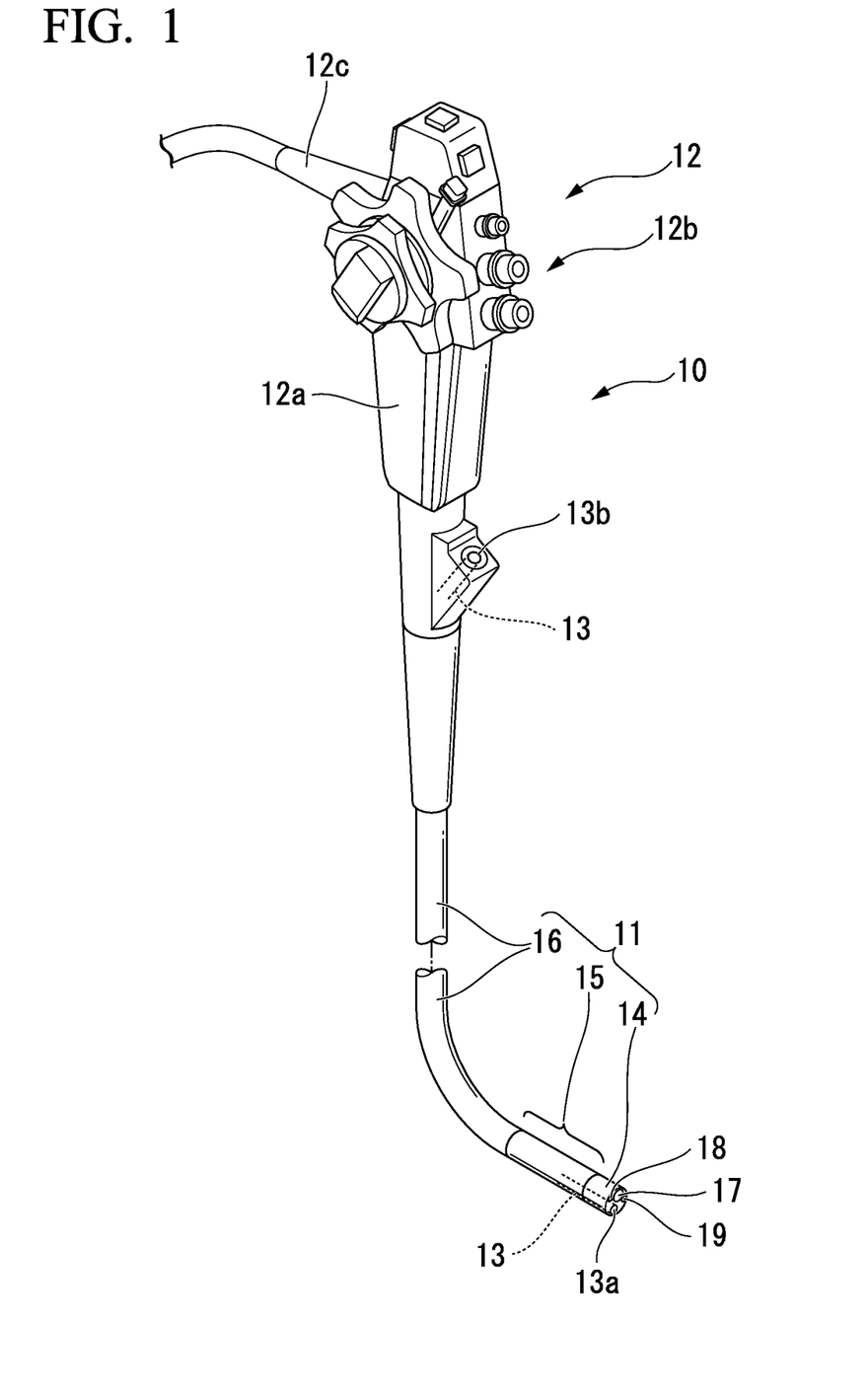
FIG. 1 is a view showing an overall configuration of an endoscope used for a method for dissecting a submucosal layer of one embodiment of the present invention.

FIG. 1 is a view showing an overall configuration of an endoscope used for a method for dissecting a submucosal layer according to one embodiment of the present invention. As shown FIG. 1, an endoscope 10 used in the present embodiment includes an insertion portion 11 and a manipulation portion 12.

The insertion portion 11 is flexible and is formed in a tubular shape, and is inserted into a body of a patient. A distal end part 14, a bending part 15, and a flexible tube part 16 are provided in the insertion portion 11 in order from a distal end of the endoscope 10. A treatment instrument insertion channel 13 into which a treatment instrument is inserted is provided along a longitudinal direction of the insertion portion 11.

The distal end part 14 is arranged in the distal end of the endoscope 10. A distal end opening portion 13a that is communicated with the treatment instrument insertion channel 13, an imaging portion 17, an illuminating portion 18, and an air supply part 19 are provided in the distal end of the distal end part 14.

The imaging portion 17 is capable of capturing a site that is an object to be treated and is illuminated by the illuminating portion 18. The imaging portion 17 is capable of capturing the treatment instrument in a state where the treatment instrument is protruded from the distal end opening portion 13a of the treatment instrument insertion channel 13. That is, the treatment instrument that is inserted into the treatment instrument insertion channel 13 is capable of being projected from the distal end opening portion 13a and being retracted into the treatment instrument insertion channel 13, the distal end of the treatment instrument is capable of being advanced into the imaging field of view of the imaging portion 17, and the distal end of the treatment instrument is captured by the imaging portion 17.

The air supply part 19 is capable of supplying such as an air in accordance with a manipulation of the manipulation portion 12.

The bending part 15 is provided in a proximal end of the distal end part 14. The bending part 15 is configured so as to be capable of bending to turn the distal end part 14 and bends in accordance with a manipulation of the manipulation portion 12.

The flexible tube part 16 is a tubular part that are connected with the bending part 15 and the manipulation portion 12. The flexible tube part 16 includes, for example, a corrugated tube that a band member made of a metal or a resin is wound and a soft outer resin.

The manipulation portion 12 is connected with a proximal end of the flexible tube part 16. The manipulation portion 12 includes a grip 12a, an input part 12b, a universal cord 12c, and a proximal end opening portion 13b of the treatment instrument insertion channel 13. The grip 12a is a grasped part by an operator. The input part 12b receives an input manipulation to bend the bending part 15 and an input manipulation to supply the air from the air supply part 19. The universal cord 12c outputs an image captured by the imaging portion 17 to an outside. The universal cord 12c is capable of connecting with a display apparatus such as a liquid crystal display via an image processing apparatus such as a processor.

The proximal end opening portion 13b is communicated with the treatment instrument insertion channel 13. The treatment instrument such as a local injection device, a high frequency knife, a grasping tool, a scissor forceps, and a needle forceps is inserted into the proximal end opening portion 13b of the manipulation portion 12, the treatment instrument is inserted into an inner side of the treatment instrument insertion channel 13, and is protruded from the distal end opening portion 13a of the distal end portion 14.

Next, a site of the gastrointestinal tract 1 into which the endoscope 10 is inserted and is to be treated will be described by a method for dissecting a submucosal layer according to the present embodiment.

Figure 2:
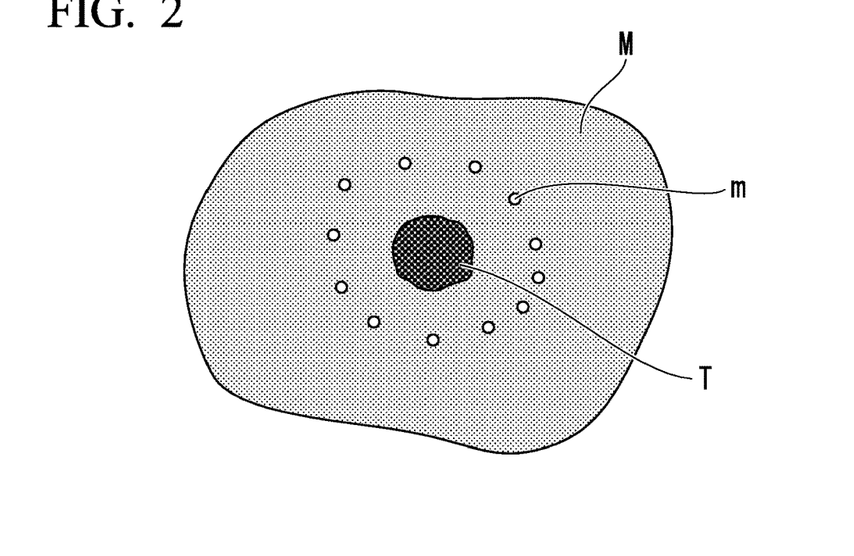
FIG. 2 is a plan view showing a gastrointestinal tract which is treated and into which an endoscope is inserted in the method for dissecting a submucosal layer.
Figure 3:
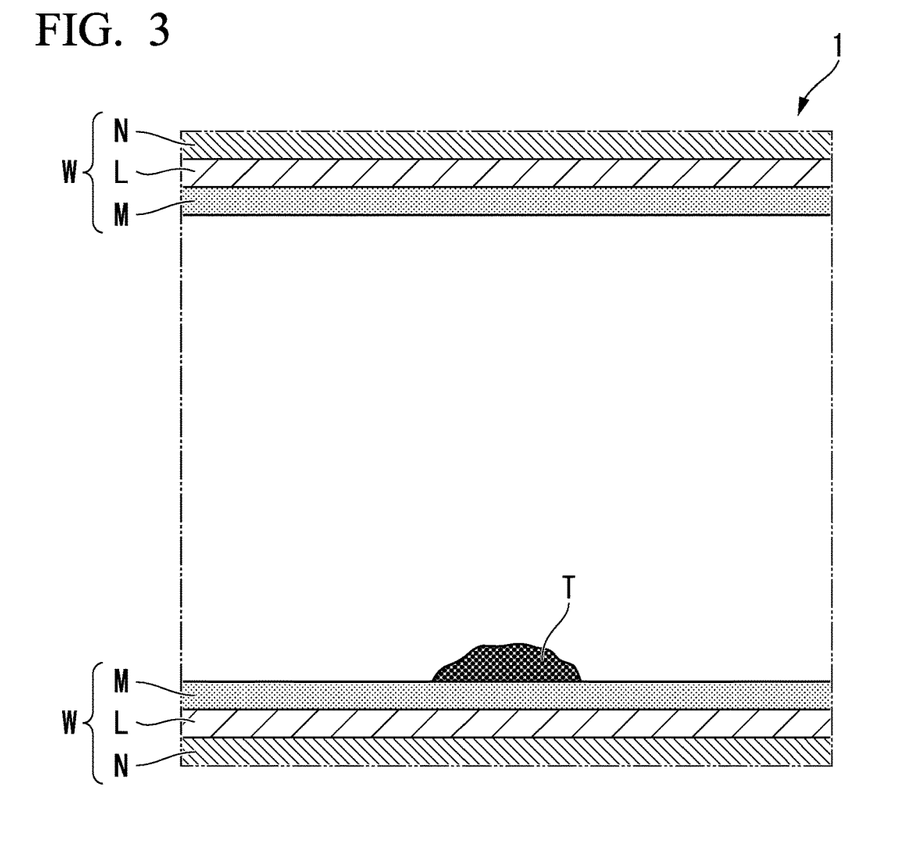
FIG. 3 is a cross-sectional view showing the gastrointestinal tract which is treated and into which an endoscope is inserted in the method for dissecting a submucosal layer.

FIG. 2 is a plan view showing the gastrointestinal tract 1 which is treated and into which the endoscope 10 is inserted in the method for dissecting a submucosal layer. FIG. 3 is a cross-sectional view showing the gastrointestinal tract 1 which is treated and into which the endoscope 10 is inserted in the method for dissecting a submucosal layer.

The gastrointestinal tract 1 is, for example, an esophagus, a stomach, a small intestine, a large intestine or the like. A tract wall W of the gastrointestinal tract 1 includes at least a mucosal layer M, a submucosal layer L, and a muscle layer N and the mucosal layer M, the submucosal layer L, and the muscle layer N are positioned in order from an inside of an organ lumen to an outside of the organ lumen.

As shown in FIG. 2 and FIG. 3, a lesion T is formed in a portion of the gastrointestinal tract 1. In a thickness direction of the tract wall W, there is a case where the lesion T is formed only in the mucosal layer M or there is a case where the lesion T is formed only in the submucosal layer L.

When the treatment instrument is started using the method for dissecting a submucosal layer, a position and an area of the lesion T can be clarified by, for example, spraying a dye for the operator to accurately diagnose the position and the area of the lesion T. Because a finely concavity and convexity of the lesion T are shown up by spraying the dye and the dye of the lesion T is decolorized with the time course, the position and the area of the lesion T can be clarified.

The operator marks the mucosal layer M surrounding of the area including the lesion T using the known method after accurately diagnosing the position and the area of the lesion T. As shown in FIG. 2, a plurality of marks m are marked surrounding the lesion 1' in outward from an outer circumference of the lesion T. A known treatment instrument can be used for marking. For example, a treatment instrument such as an electric scalpel is used by being inserted into the treatment instrument insertion channel 13 of the endoscope 10.

Next, a method for dissecting a submucosal layer will be described in detail.

[Incising Step]

The operator performs the incising step.

Figure 4:
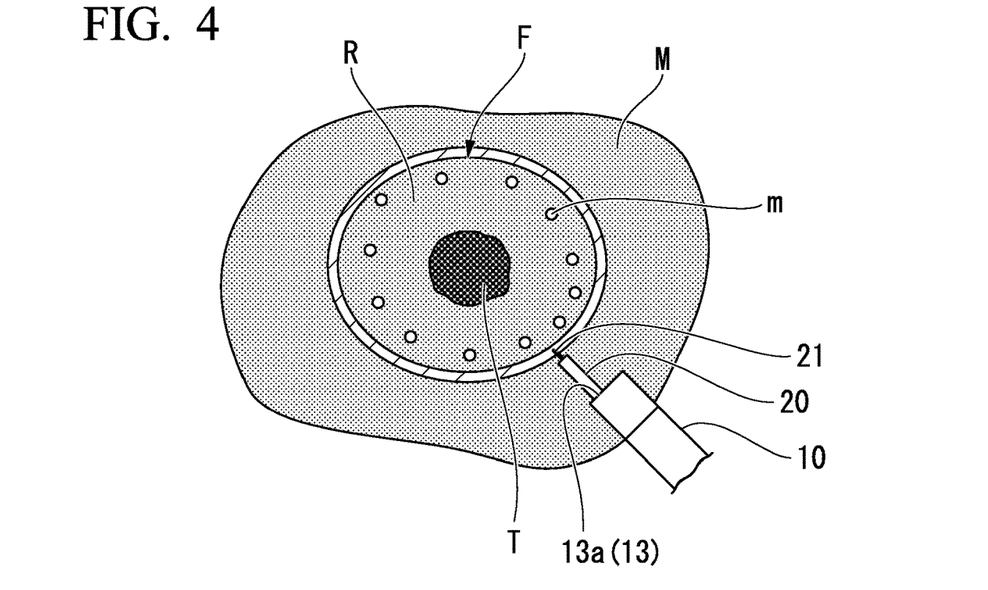
FIG. 4 is a plan view showing an incising step of the method for dissecting a submucosal layer.
Figure 5:
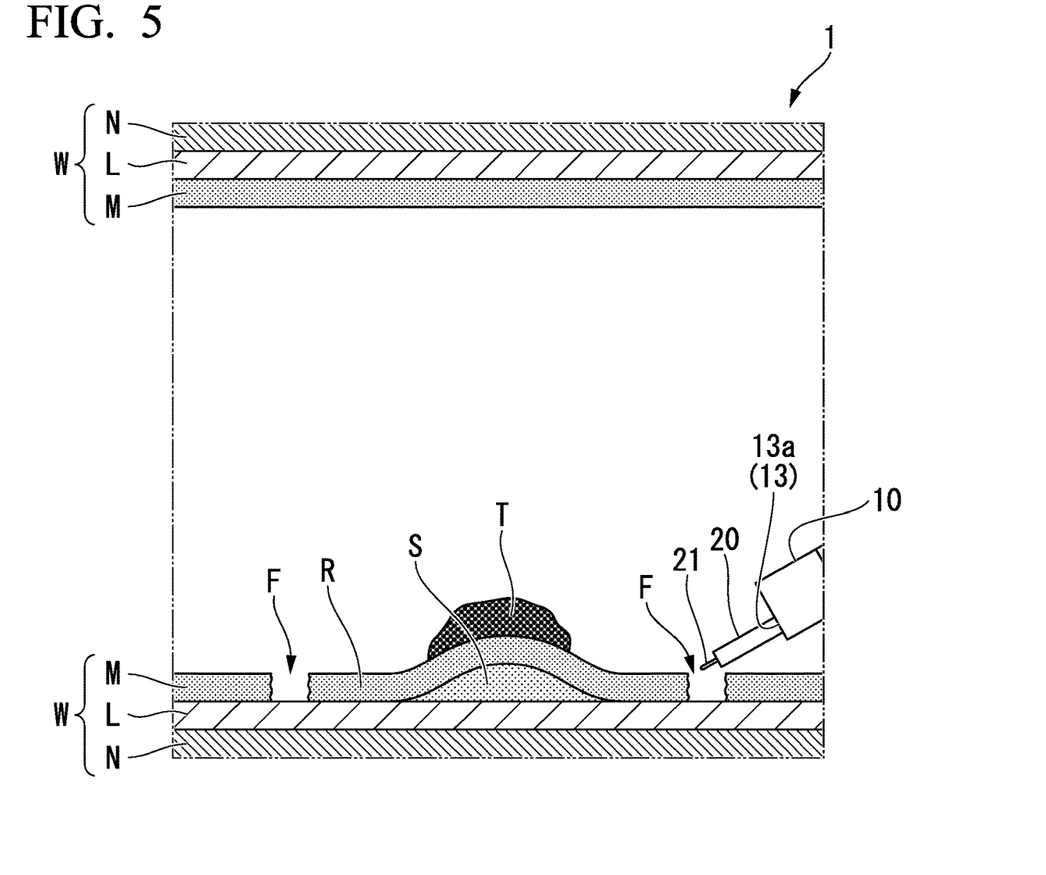
FIG. 5 is a cross-sectional view showing the incising step of the method for dissecting a submucosal layer.

FIG. 4 is a plan view showing an incising step of the method for dissecting a submucosal layer according to the present embodiment. FIG. 5 is a cross-sectional view showing the incising step of the method for dissecting a submucosal layer according to the present embodiment.

The lesion T is bulged by injecting a saline S or the like to the submucosal layer T before the operator starts the incising step as necessary. A known treatment instrument can be used for injecting the saline S or the like. For example, a treatment instrument including a local injection needle that is capable of discharging the saline S or the like is used by being inserted into the treatment instrument insertion channel 13 of the endoscope 10. The local injection needle is protruded from the distal end opening portion 13a of the treatment instrument insertion channel 13 and inserted into the mucosal layer M. In this time, although an insertion depth of the local injection needle passed through the mucosal layer M, the insertion depth does not reach the muscle layer N and a distal end of the local injection needle is arranged on the submucosal layer L. The operator discharges the saline S or the like from the distal end of the local injection needle, and, as shown in FIG. 5, the lesion T is bulged.

The operator incises at least a portion of the mucosal layer M (tissue) surrounding the area including the lesion T in the gastrointestinal tract 1 (incising step). As shown in FIG. 4, the operator incises the mucosal layer M surrounded by the plurality of marks m. A known treatment instrument can be used for incising the mucosal layer M. For example, a high frequency knife 20 including a needle knife 21 is used by inserting into the treatment instrument insertion channel 13 of the endoscope 10. The high frequency knife 20 is protruded from the distal end opening portion 13a of the treatment instrument insertion channel 13 and the mucosal layer M is incised by contacting the needle knife 21 currying current with the mucosal layer M by the operator. In order to reliably remove without remaining the lesion T, the mucosal layer M surrounding the area including the lesion T is incised. The operator incises the mucosal layer M along a circumference of an area R defined by connecting the plurality of marks m that are formed around the area including the lesion T.

An incising portion F is formed around the area including the lesion T by performing the incising step.

As shown in FIG. 4 and FIG. 5, although the mucosal layer M is incised along the entire circumference of the area R and the incising portion F is formed, a range (length) of the incising portion F is not limited to this. At least a portion of the mucosal layer M of a side in which the dissection of the submucosal layer L (to be described later) is started may be incised, the range of the incising portion F may be half of the entire circumference, and the range of the incising portion F may be nearly one-quarter of the entire circumference. An optimum incising range can be selected in accordance with the position and the size of the lesion T.

[Fixing Step]

The operator performs the fixing step after the incising step.

Figure 6:
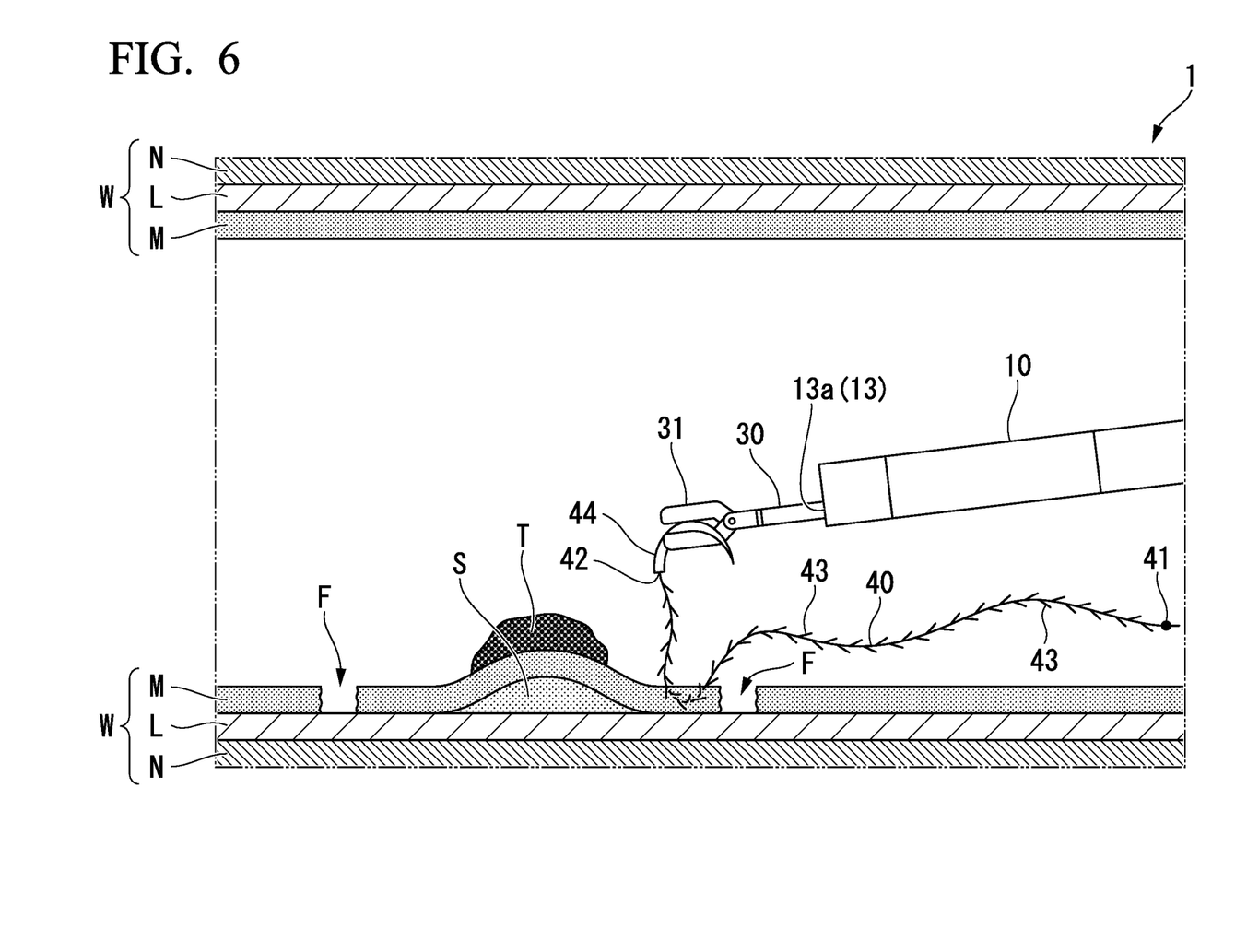
FIG. 6 is a cross-sectional view showing a fixing step of the method for dissecting a submucosal layer.

FIG. 6 is a cross-sectional view showing a fixing step of the method for dissecting a submucosal layer according to the present embodiment.

The operator fixes one end of a suture thread 40 to the area including the lesion T using a needle holder 30 (grasping instrument), the suture thread 40, and a needle 44 (fixing step).

As shown in FIG. 6, the suture thread 40 includes a first end 41 having a knot having a predetermined size, a second end 42 to which the needle 44 is connected, and a plurality of barbs 43 that are arranged along a longitudinal axis between the first end 41 and the second end 42.

The needle holder 30 including a grasping portion 31 is inserted into the treatment instrument insertion channel 13 of the endoscope 10 and is protruded from the distal end opening portion 13a. A known treatment instrument can be used for the needle holder 30.

The needle 44 that is connected with the second end 42 of the suture thread 40 is grasped by the grasping portion 31 of the needle holder 30 that is protruded from the distal end opening portion 13a.

As shown in FIG. 6, the operator manipulates the needle holder 30 grasping the needle 44, and the needle 44 is inserted into the tract wall W (tissue) of the area including the lesion T and the operator puts a stitch. More specifically, the needle 44 is inserted into the mucosal layer M that is the area between the lesion T and the incising portion F and is the area vicinity of the endoscope 10. Although, as shown in FIG. 6, the needle 44 is inserted into only the mucosal layer M among the tract wall W, the needle 44 may be inserted into both the mucosal layer M and the submucosal layer L at the depth that does not reach the muscle layer L.

Figure 7A:
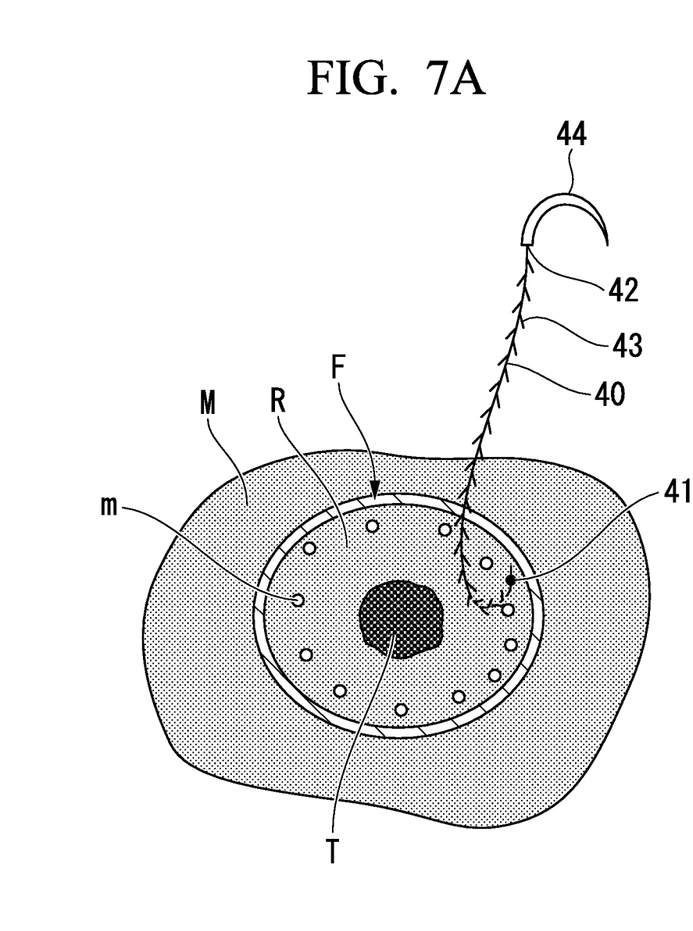
FIG. 7A is a schematic diagram showing the fixing step of the method for dissecting a submucosal layer.
Figure 7B:
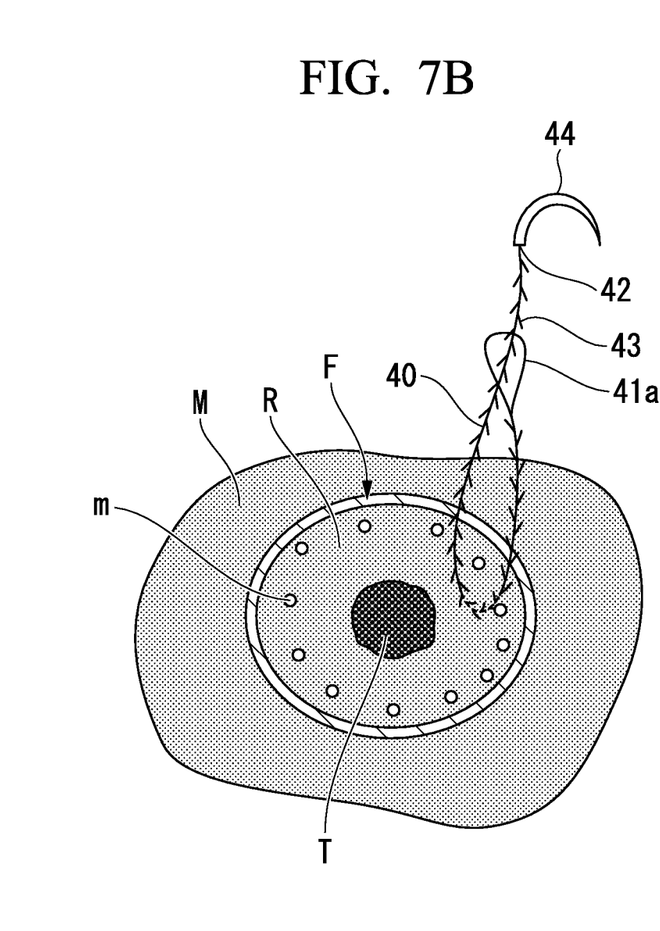
FIG. 7B is a schematic diagram showing the fixing step of the method for dissecting a submucosal layer.

FIG. 7A and FIG. 7B are schematic diagram showing the fixing step of the method for dissecting a submucosal layer according to the present embodiment, the method for fixing are different from each other.

The plurality of barbs 43 is formed along the longitudinal axis of the suture thread 40 between the first end 41 and the second end 42 of the sure thread 40. Thereby, the sure thread 40, in an inside of the mucosal layer M (tract wall W), is capable of moving in a moving direction of the needle 44 and is not capable of moving in a direction opposed to the moving direction of the needle 44 by engaging the plurality of barbs 43 with the mucosal layer M (tract wall W).

As shown in FIG. 7A, the needle 44 is inserted into the mucosal layer M (tract wall W) of the area between the lesion T and the incising portion F and the operator puts a stitch. The needle 44 is pulled into the gastrointestinal tract 1 until the first end 41 including the knot formed in advance arrives the mucosal layer M that configures the tract wall W. In a state where the first end 41 of the sure thread 40 is contacted with the mucosal layer M that configures the tract wall W, the first end 41 of the suture thread 40 cannot move in the moving direction of the needle 44 because the knot of the first end 41 becomes an anchor. Furthermore, the first end 41 of the sure thread 40 cannot move in the direction opposed to the moving direction of the needle 44 because the plurality of barbs 43 of the suture thread 40 engage on the mucosal layer M (tract wall W). That is, the first end 41 of the suture thread 40 can be fixed by inserting the needle 44 connected with the second end 42 of the suture thread 40 into the tract wall W of the area including the lesion T.

A shape of the first end 41 of the suture thread 40 is not limited to the knot that is formed in advance. For example, as shown in FIG. 7B, the first end 41a of the suture 40 is a loop shape, after the needle 44 is inserted into the mucosal layer M (tract wall W) of the area between the lesion T and the incising portion F and the operator puts a stitch, the first end 41a of the suture thread 40 can be fixed to the tract wall W of the area including the lesion T by passing the needle 44 through the loop of the first end 41a of the suture thread 40.

The first end of the suture thread 40 can be fixed to the tract wall W of the area including the lesion T by attaching an anchor member that is a plate shape to the first end of the suture thread 40.

[Piercing Step]

The operator performs the piercing step after the fixing step.

Figure 8:
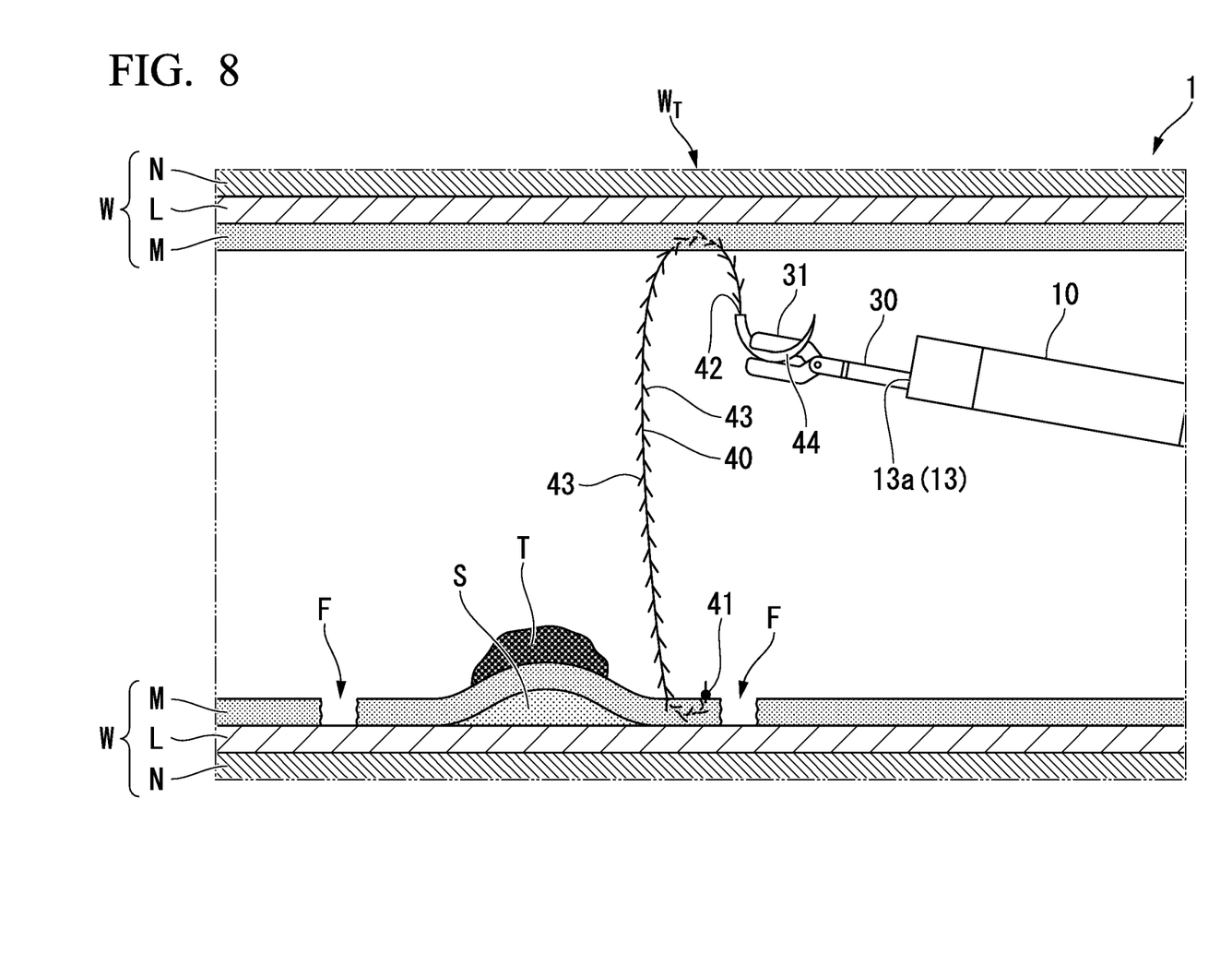
FIG. 8 is a cross-sectional view showing a piercing step of the method for dissecting a submucosal layer.

FIG. 8 is a cross-sectional view showing a piercing step of the method for dissecting a submucosal layer according to the present embodiment.

The operator inserts the needle 44 into the tract wall $W_t$ that faces the area including the lesion T and the suture thread 40 inserting into the tract wall $W_t$ is pulled into the gastrointestinal tract 1 (piercing step).

As shown in FIG. 8, the operator manipulates the needle holder 30 grasping the needle 44, the needle 44 is inserted into the tract wall $W_t$ (mucosal layer M) facing the area including the lesion T and the operator puts a stitch, and the needle 44 and the suture thread 40 are pulled into the gastrointestinal tract 1 from the tract wall $W_t$. As shown in FIG. 8, the needle 44 is inserted into only the mucosal layer M among the tract wall $W_t$, the needle 44 may be inserted into both the mucosal layer M and the submucosal layer L at the depth that does not reach the muscle layer L.

The tract wall $W_t$ that faces the area including the lesion T is not limited to the tract wall $W_t$ that faces the area including the lesion T. A position that faces the area including the lesion T includes a position of an upside and a front, a position of an upside and a rear, and a position of an upside and a lateral. As described later, when the needle 44 or the suture thread 40 is pulled and at least a portion of the area including the lesion T is lifted, the tract wall W which is positioned at a passing point that is capable of changing a pulling force into a lifting force is included in the tract wall $W_t$ that faces the area including the lesion T.

[Lifting Step] (First Engaging Step)

The operator performs the lifting step (first engaging step) after the piercing step.

Figure 9:
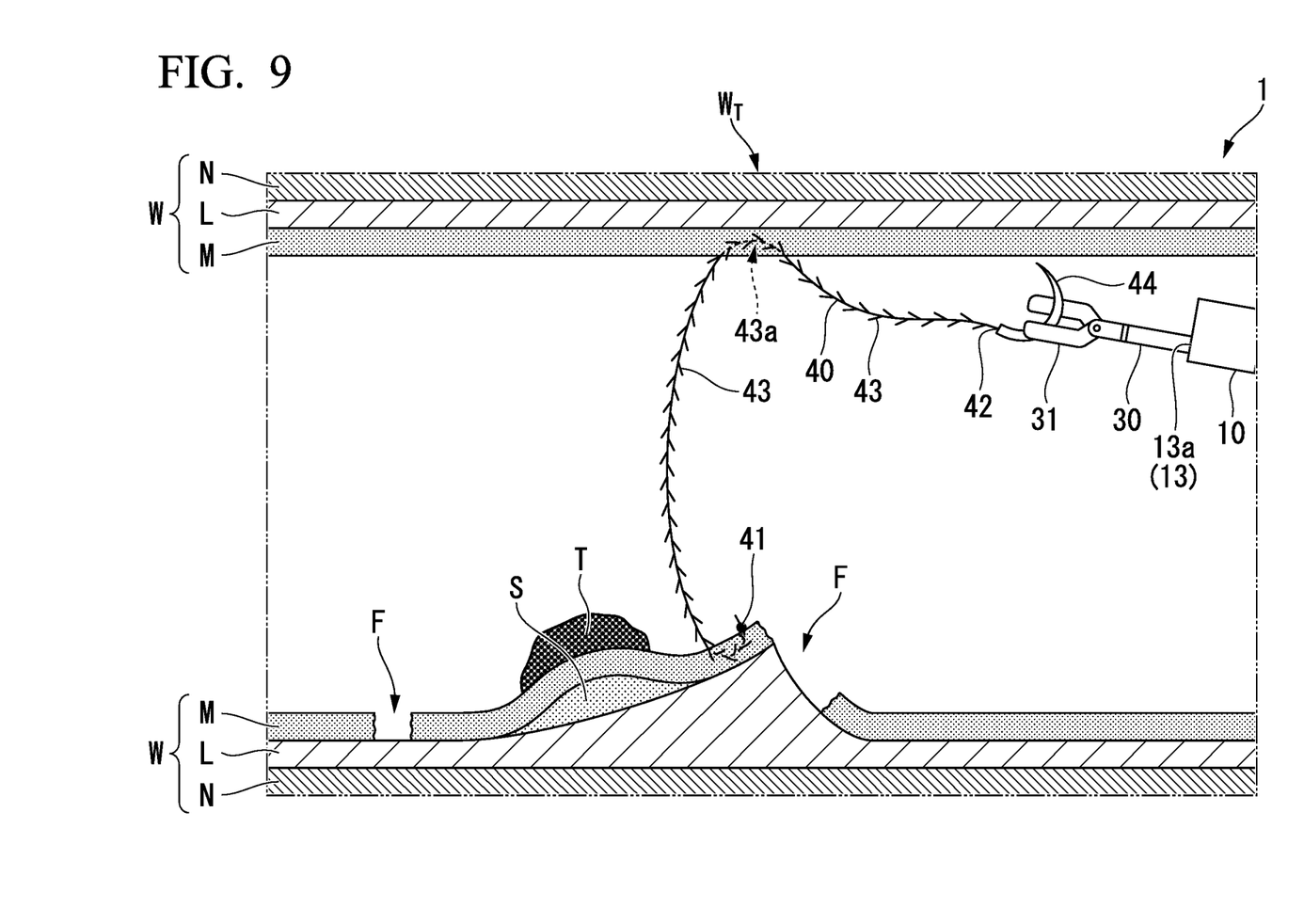
FIG. 9 is a cross-sectional view showing a lifting step (first engaging step) of the method for dissecting a submucosal layer.

FIG. 9 is a cross-sectional view showing a lifting step (first engaging step) of the method for dissecting a submucosal layer according to the present embodiment.

In the piercing step, the operator pull the needle 44 or the suture thread 40 into the gastrointestinal tract 1 from the tract wall $W_t$, at least a portion of the area including the lesion T is lifted, and engages the plurality of barbs 43 of the suture thread 40 with the tract wall W. Thereby, a state where at least a portion of the area including the lesion T is lifted is hold (lifting step).

As shown in FIG. 9, the operator grasps and pulls the needle 44 or the suture thread 40 into the gastrointestinal tract 1 from the tract wall $W_t$ using the grasping portion 31 of the needle holder 30 or the grasping instrument, and lifts at least a portion of the area including the lesion T to which the first end 41 of the suture thread 40.

As described above, the plurality of barbs 43 that are arranged along a longitudinal axis of the suture thread 40 between the first end 41 and the second end 42 of the suture thread 40. Thereby, the sure thread 40, in an inside of the tract wall $W_T$(mucosal layer M), is capable of moving in a moving direction of the needle 44 and is not capable of moving in a direction opposed to the moving direction of the needle 44 by engaging with the tract wall $W_T$. That is, a state where at least a portion of the area including the lesion T is lifted can be hold by engaging a first barb 43a among the plurality of barbs 43 of the suture thread 40 with the tract wall $W_T$ that faces the area including the lesion T (the first engaging step).

In accordance with the position of the area including the lesion T or a posture of the patient, the tract wall $W_T$ that faces the area including the lesion T is appropriately selected and the needle 44 is inserted, and the barb 43a of the suture thread 40 is engaged with the tract wall $W_T$. Thereby, the operator can lift at least a portion of the area including the lesion T. Furthermore, the operator can adjust at least a portion of a lifting degree (amount of lift) of the area including the lesion T by adjusting a pulling degree (amount of pull) of the needle 44 or the suture thread 40 that is pulled into the gastrointestinal tract 1 from the tract wall $W_T$. That is, without causing by the position of the lesion T or the posture of the patient, the operator can add the appropriate traction to the dissection part of the area including the lesion T. Furthermore, the operator only manipulates to insert the suture thread 40 attaching the plurality of barbs 43 into the tract wall $W_T$ and pull. Thereby, a state where the portion of the area including the lesion T, the appropriate traction is added to the dissection part, and the portion of the area including the lesion T by the first barb 43a can be hold. Consequently, it can be easy for the operator to add the appropriate traction to the dissection part of the area including the lesion T.

In the lifting step, in addition to the traction by the above mentioned the suture thread 40, the operator may fine-adjust at least a portion of the amount of lift of the area including the lesion T by additionally adjusting an amount of air supply into the gastrointestinal tract 1. The operator manipulates the manipulation portion 12 of the endoscope 10 and supplies the air or the like from the air supply part 19 in order to secure an operational field in gastrointestinal tract 1. The operator can fine-adjust a distance between the tract wall W of the area including the lesion T and the tract wall $W_T$ that faces the tract wall W (distance of the tract walls) by adjust the amount of air supply from the air supply part 19. In addition to the amount of pull of the needle 44 or the suture thread 40, the operator can fine-adjust the traction adding to the dissection part of the area including the lesion T by adjusting the amount of air supply into the gastrointestinal tract 1.

[Dissecting Step]

The operator performs the dissecting step after the end of the lifting step (first engaging step).

Figure 10:
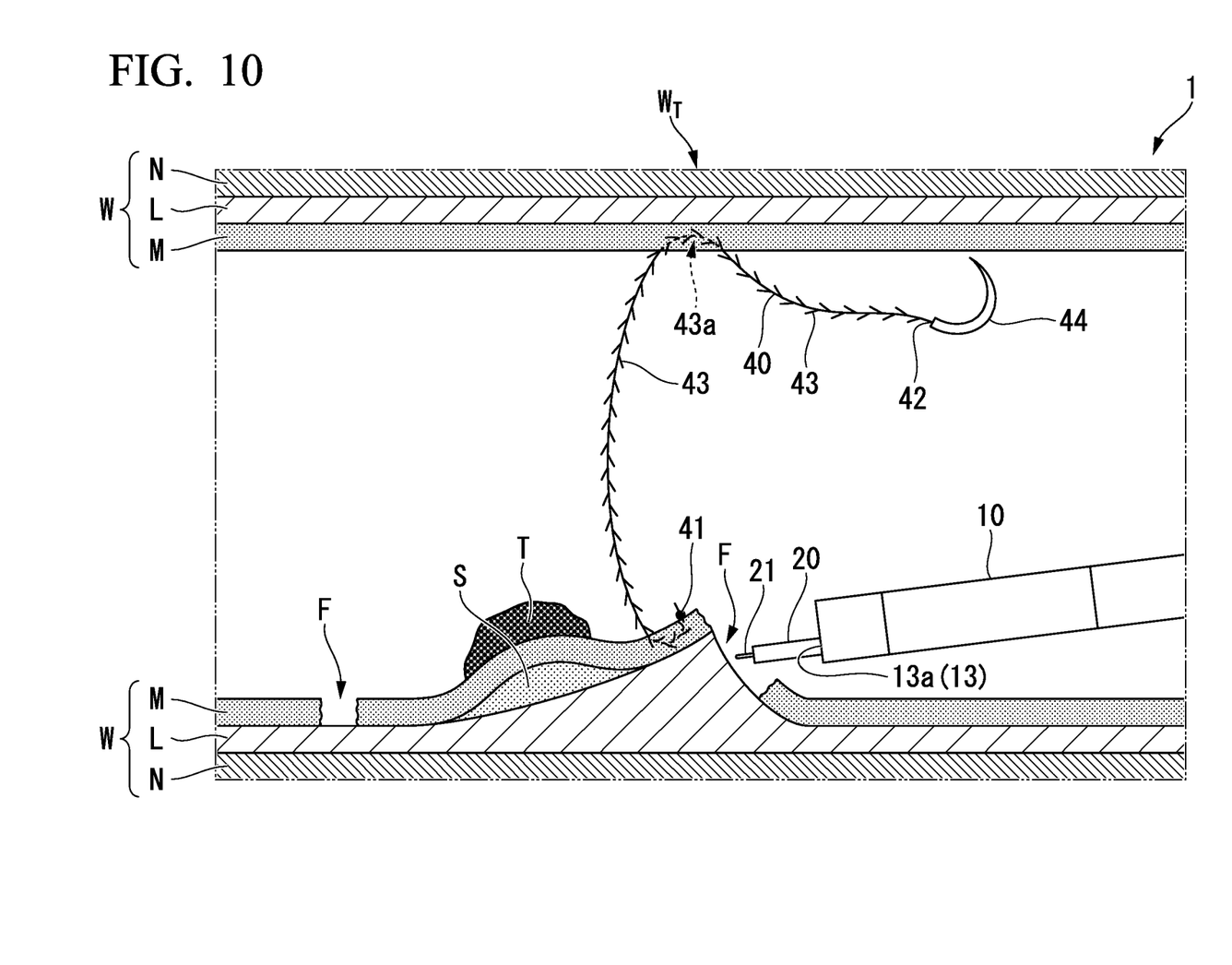
FIG. 10 is a cross-sectional view showing a dissecting step of the method for dissecting a submucosal layer

FIG. 10 is a cross-sectional view showing a dissecting step of the method for dissecting a submucosal layer according to the present embodiment.

The operator dissects the submucosal layer L of the gastrointestinal tract 1 in a state where at least the portion of the area including the lesion T is lifted (dissecting step)

As shown in FIG. 10, the operator releases the needle 44 or the suture thread 40 from the needle holder 30 or grasping instrument and lifts the suture thread 40 after at least the portion of the area including the lesion T. Even in this case, a state where at least the portion of the area including the lesion T is lifted is hold because the first barb 43*a* among the plurality of barbs 43 of the suture thread 40 is engaged with the tract wall $W_T$ that faces the area including the lesion T. The submucosal layer L widely expands toward a side in which the endoscope 10 is positioned because the state where at least the portion of the area including the lesion T is lifted is hold (the appropriate traction is added to the dissection part of the area including the lesion T).

The operator inserts the high frequency knife 20 including a needle knife 21 into the treatment instrument insertion channel 13 of the endoscope 10, and the high frequency knife 20 is protruded from the distal end opening portion 13*a*. The operator dissects the submucosal layer L by contacting the high frequency knife 20 including a needle knife 21 that is protruded from the distal end opening portion 13*a* with the submucosal layer L and currying the current.

The appropriate traction is added to the dissection part of the area including the lesion T, the operator can secure the submucosal layer L in the field of the endoscope 10 and can smoothly and reliably dissect the submucosal layer L.

[Lifting Step] (Second Engaging Step)

The operator performs a lifting step additionally in accordance with a procedure of the dissecting step.

Figure 11:
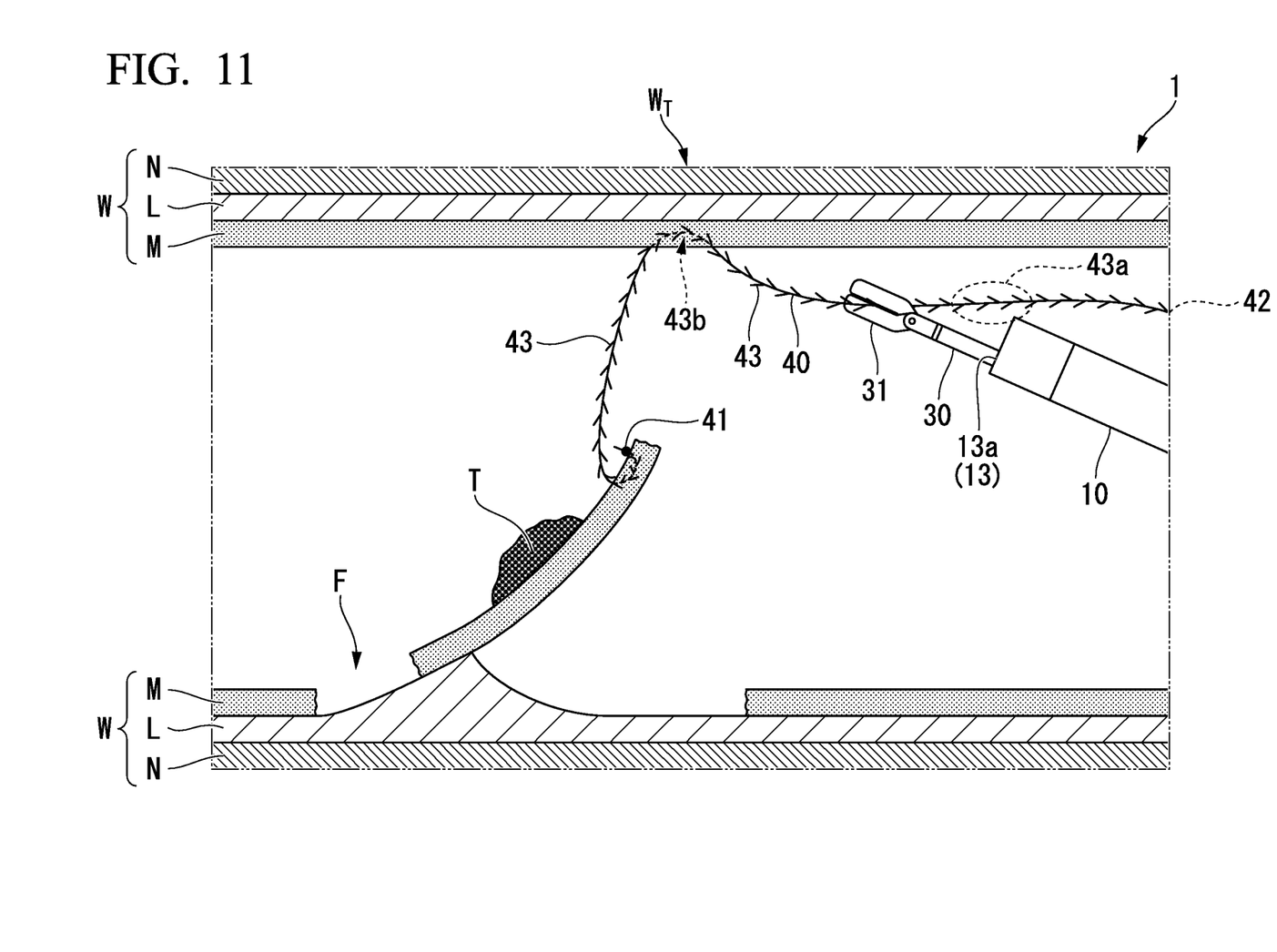
FIG. 11 is a cross-sectional view showing a lifting step (second engaging step) of the method for dissecting a submucosal layer.

FIG. 11 is a cross-sectional view showing a lifting step (second engaging step) of the method for dissecting a submucosal layer according to the present embodiment.

The operator holds the state of lifting at least the portion of the area including the lesion (first engaging step) and proceeds to dissect the submucosal layer L (dissecting step) by engaging the first barb 43*a* among the plurality of barbs 43 of the suture thread 40 with the tract wall $W_T$ that faces the area including the lesion T. As the dissection of the submucosal layer L proceeds, it is difficult for the operator to secure in the field of the endoscope 10.

In this case, the operator performs the lifting step (second engaging step) additionally. As described above, the plurality of barbs 43 that are arranged along a longitudinal axis of the suture thread 40 between the first end 41 and the second end 42 are formed and the first barb 43*a* is formed in the suture thread 43. Furthermore, as shown in FIG. 11, the plurality of barbs 43 includes a second barb 43*b* that is provided closer to the first end 41 of the suture thread 40 than the first barb 43*a*.

After the operator dissects the submucosal layer L that is lifted in the first engaging step, the operator pulls the needle 44 or the suture thread 40 that is pulled into the gastrointestinal tract 1 from the tract wall $W_T$. Continuously, the operator can hold in a state of further lifting the portion of the area including the lesion T than a position at the time of the first engaging step by engaging the second barb 43*b* among the plurality of barbs 43 with the tract wall $W_T$ that is positioned so as to face the area including the lesion T (second engaging step).

As shown in FIG. 11, the operator inserts the needle holder 30 including the grasping portion 31 into the treatment instrument insertion channel 13 of the endoscope 10 and the needle holder 30 is protruded from the distal end opening portion 13*a*. The operator grasps and pulls the needle 44 or the suture thread 40 that is pulled into the gastrointestinal tract 1 from the tract wall $W_T$ using the grasping portion 31 of the needle holder 30 or the grasping instrument and further lifts at least the portion of the area including the lesion T to which the first end 41 of the suture thread 40 is fixed. The operator can hold in a state of further lifting the portion of the area including the lesion T than a position at the time of the first engaging step by engaging the second barb 43*b* among the plurality of barbs 43*b* of the suture thread 40 with the tract wall $W_T$.

The lifting step includes the first engaging step and the second engaging step that is performed after the first engaging step. The second engaging step performs to pull the needle 44 or the suture thread 40 pulled into the gastrointestinal tract 1 from the tract wall $W_T$ and to hold in a state of further lifting the portion of the area including the lesion T than a position at the time of the first engaging step. That is, in the method for dissecting a submucosal layer, in the lifting step, at least the portion of the amount of lift of the area including the lesion T is increased by increasing the amount of pull of the needle 44 or the suture thread 40 that is pulled into the gastrointestinal tract 1 in accordance with the position at which the submucosal layer L is dissected.

As with the first engaging step, in the second engaging step, the operator may fine-adjust the amount of lift of at least the portion of the area including the lesion T (appropriate traction to a dissection part of the area including the lesion T) by furthermore adjusting the amount of air supply to the gastrointestinal tract 1 in addition to the adjustment of the traction by the above mentioned the suture thread 40.

[Dissection Step]

The operator perform the dissection step additionally after the end of the lifting step (second engaging step).

Figure 12:
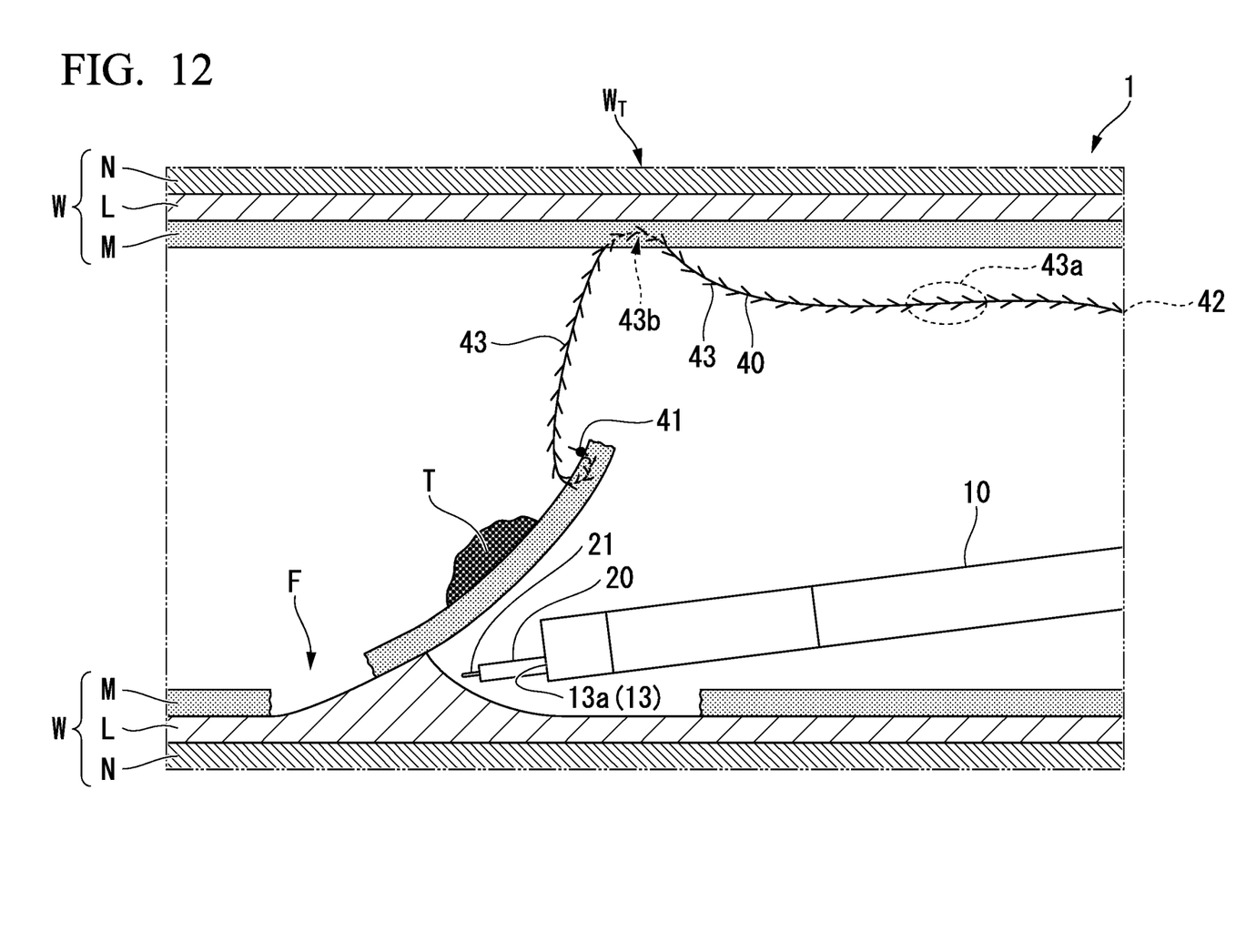
FIG. 12 is a cross-sectional view showing a dissection step of the method for dissecting a submucosal layer.

FIG. 12 is a cross-sectional view showing a dissection step of the method for dissecting a submucosal layer according to the present embodiment.

The operator dissects the submucosal layer L of the gastrointestinal tract 1 in the state of further lifting the portion of the area including the lesion T than a position at the time of the first engaging step (dissection step).

As shown in FIG. 12, the operator releases the needle holder 30 or the grasping instrument from the needle 44 or the suture thread 40 after further lifting the portion of the area including the lesion T than a position at the time of the first engaging step. Even in this case, the state of further lifting the portion of the area including the lesion T than a position at the time of the first engaging step is held because the second barb 43*b* among the plurality of barbs 43 of the suture thread 40 is engaged with the tract wall $W_T$ that faces the area including the lesion T. The submucosal layer L widely expands toward a side in which the endoscope 10 is positioned because the state of further lifting the portion of the area including the lesion T than a position at the time of the first engaging step is held (the appropriate traction is added to the dissection part of the area including the lesion T).

The high frequency knife 20 including a needle knife 21 is used by inserting into the treatment instrument insertion channel 13 of the endoscope 10 by the operator and the high frequency knife 20 is protruded from the distal end opening portion 13*a*. The submucosal layer L is dissected by contacting the needle knife 21 of the high frequency knife 20 that is protruded from the distal end opening portion 13*a* with the submucosal layer L and currying the current by the operator.

The appropriate traction is added to a dissection part of the area including the lesion T, the operator can capture the submucosal layer L in the field of the endoscope 10 and can smoothly and reliably dissect the submucosal layer L.

Conventionally, in the dissection of the submucosal layer, the method using the clip with the thread and the traction clip is known as the method of adding the traction to the dissection part. The method using the clip with thread includes fixing the clip of the clip with thread to the mucosal layer of the dissection part at which the operator wants to add the traction and the traction is added to the dissection part by pulling the thread of the clip with the thread from a mouth side or an anus side using a weight. The method using the traction clip includes fixing the traction clip to a first mucosal layer of the dissection part to which the operator wants to add the traction and a second mucosal layer that faces the first mucosal layer respectively, and adding the traction to the dissection part by connecting two traction clips by a spring.

In the method using the clip with the thread, a pulling direction of the thread of the mucosal layer cannot be adjusted in accordance with the position of the lesion because the pulling direction of the thread is the mouth side or the anus side constantly, and it is difficult to add the appropriate traction to the dissection part. A fine adjustment of the traction by an amount of air supply is impossible because a facing wall that faces the lesion is not used.

In the method using the traction clip, an amount of traction depends to an inherent pull force of the spring because the traction is added to the dissection part by elasticity of the spring connecting the traction clips. Therefore, it is difficult to appropriately set the amount of the traction to the dissection part in accordance with the position of the lesion. The operation of the dissection is cumbersome because it is necessary to vary the fixing position of the traction clip, to change the spring, and to pull the dissection part from the early stage by comparatively large force using the spring with a procedure of the dissection of the submucosal layer.

The method for dissecting a submucosal layer according to the present embodiment is to solve the above problem in the method using the clip with the thread, the traction clip or the like.

In accordance with the position of the area including the lesion T or a posture of the patient, the tract wall $W_T$ that faces the area including the lesion T is appropriately selected and the needle 44 is inserted, and the plurality of barb 43 of the suture thread 40 is engaged with the tract wall $W_T$. Thereby, the operator can lift at least a portion of the area including the lesion T. The operator pulls the needle 44 or the suture thread 40 that is pulled into the gastrointestinal tract 1 from the tract wall $W_T$ that faces the area including the lesion T and can adjust the amount of lift of at least the portion of the area including the lesion T in accordance with that the amount of pull.

Furthermore, the operator stop pulling the needle 44 or the suture thread 40 at the timing of reaching at least the portion of the appropriate amount of lift of the area including the lesion T (at the timing of adding the appropriate traction to the dissection part of the area including the lesion) because the operator uses the suture thread 40 including the plurality of barbs 43 that are capable of engaging with the tract wall $W_T$, at the same time, the plurality of barbs that are positioned at the tract wall $W_T$ are engaged with the tract wall $W_T$ and the state where the amount of lift of at least the portion of the area including the lesion T is appropriate (appropriate traction is added to the dissection part of the area including the lesion T) can be held. That is, only the operation of passing the suture thread 40 with the plurality of barbs 43 to tract wall $W_T$ and pulling, the operator lifts at least the portion of the area including the lesion and can add the appropriate traction to the dissection part.

Furthermore, the operator proceeds the dissection of the submucosal layer L. When it is difficult to capture the submucosal layer L in the field of the endoscope 10, at least the portion of the area including the lesion is further lifted (amount of the lift is increased) and the appropriate traction can be continuously added to the dissection part of the area including the lesion T by further pulling the needle 40 and the suture thread 44 (amount of the pull is increased).

As described above, according to the method for dissecting a submucosal layer of the present embodiment, the appropriate traction can be easily and continuously added to the dissection part of the area including the lesion T and the submucosal layer L can be smoothly and reliably dissected.

[Cutting Step of Suture Thread and Suturing-Closing Step of Mucosal Defect Part]

The method for dissecting a submucosal layer of the present embodiment further includes the following step.

Figure 13:
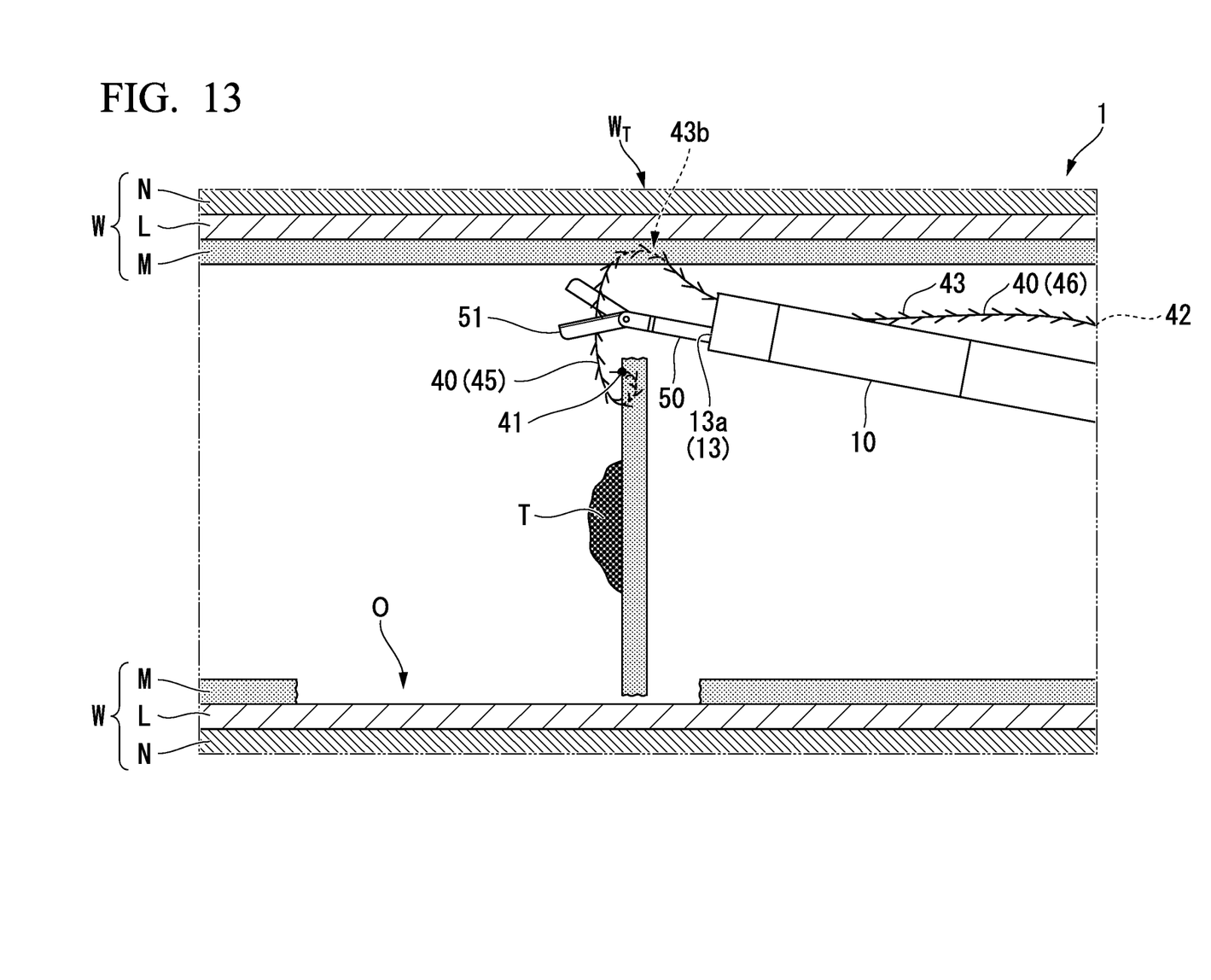
FIG. 13 is a cross-sectional view showing a cutting step of the suture thread of the method for dissecting a submucosal layer.
Figure 14:
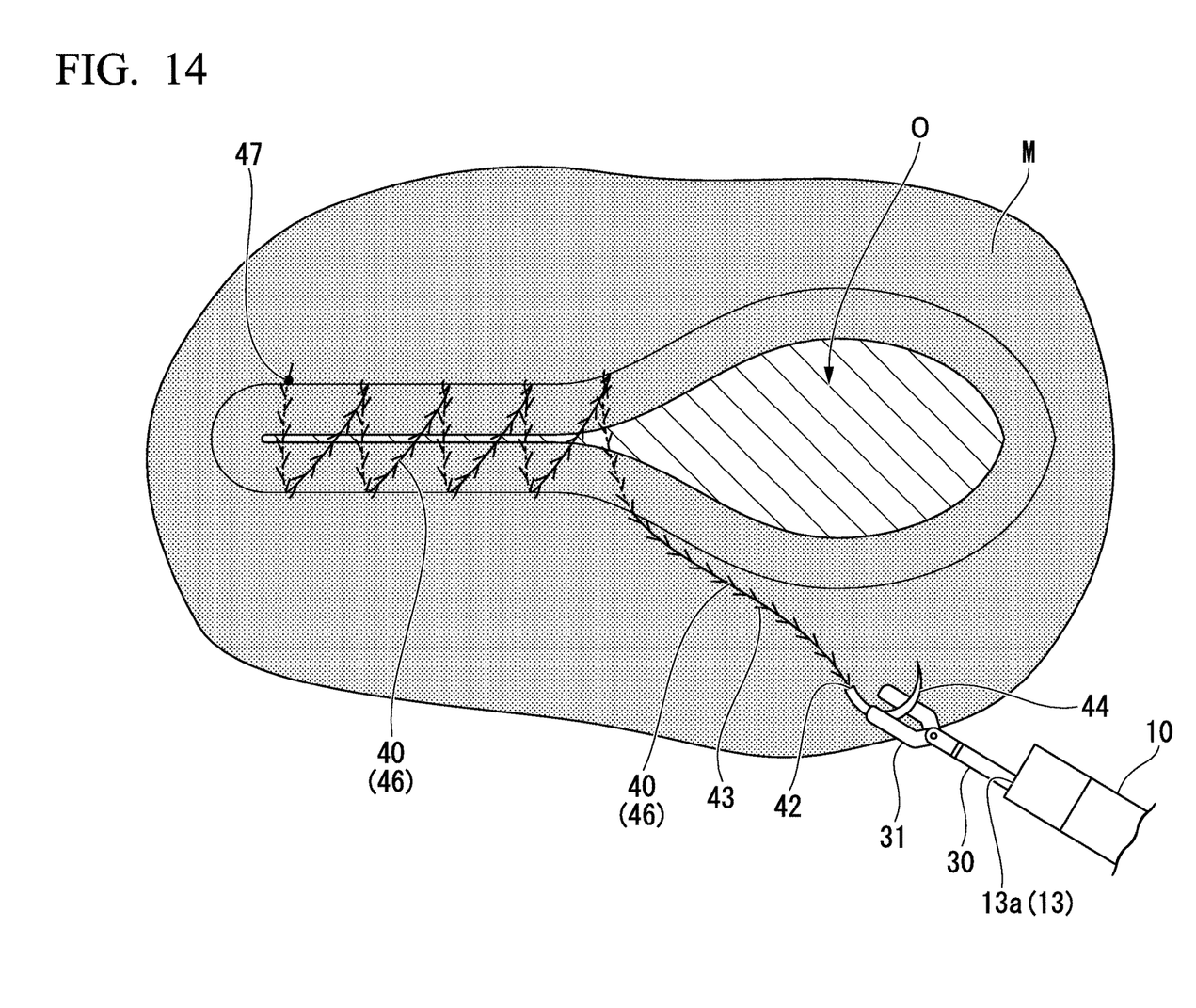
FIG. 14 is a cross-sectional view showing a suturing-closing step of a mucosal defect part of the method for dissecting a submucosal layer.

FIG. 13 is a cross-sectional view showing a cutting step of the suture thread 40 of the method for dissecting a submucosal layer. FIG. 14 is a cross-sectional view showing a suturing-closing step of a mucosal defect part O of the method for dissecting a submucosal layer.

The operator dissects the submucosal layer L and cuts the suture thread 40 at a vicinity of the area including the lesion T after separating the area including the lesion T (cutting step).

As shown in FIG. 13, the operator inserts a scissor forceps 50 including a scissor 51 into the treatment instrument insertion channel 13 of the endoscope 10 and protrudes the scissor forceps 50 from the distal end opening portion 13a. The operator can use the known scissor forceps 50.

The operator cuts the suture thread 40 in the vicinity of the area including the lesion T by the scissor 51 of the scissor forceps 50 protruded from the distal end opening portion 13a. Thereby, the suture thread 40 separates a partial suture thread 45 including the first end 41 fixed to the area including the lesion T and a remaining a suture thread 46 that fixed to the tract wall $W_T$ including the second end 42.

The operator discharges the area including the lesion T to the outside of the body and collects. The remaining thread 46 may remain in the gastrointestinal tract 1 or may discharge to the outside of the body once.

As shown in FIG. 14, the operator performs the suture thread closing that is to close the mucosal defect part using the remaining thread 46 that is picked from the tract wall $W_T$ (suturing-closing step).

The operator inserts the needle holder 30 including the grasping portion 31 into the treatment instrument insertion channel 13 of the endoscope 10 and the needle holder 30 is protruded from the distal end opening portion 13a. The operator grasps the needle 44 connected to the second end 42 of the suture thread 40 (remaining the thread 46) by the grasping portion 31 of the needle holder 30 that is protruded from the distal end opening portion 13a.

The operator puts a stitch with the needle 44 grasped by the needle holder 30 at the tissue surrounding of the mucosal defect part O and sutures the mucosal defect part O. A fixed portion 47 such as a knot that is formed in a vicinity of the end portion of the remaining thread 46 in advance is provided and the plurality of barbs 43 is formed in the remaining thread 46. Therefore, the operator can tighten the tissue surrounding the mucosal defect part O by passing the needle 44 and the remaining thread 46 through the tissue surrounding the mucosal defect part O, and can suture and close the mucosal defect part O.

It may be not necessary to suture and close the mucosal defect part O, the mucosal defect part O may is remained untouched and may be healed naturally. However, when a case where the mucosal defect part is remained untouched, because there is a report that an accidental occurrence symptom occurs with several percent probability, it is preferable to suture and close the mucosal defect part O.

The method for dissecting a submucosal layer of the present embodiment is superior in terms of a work efficiency and a cost because the mucosal defect part O can be sutured and closed using the remaining thread 46.

While the present embodiment of the present invention has been described and shown above, the present invention is not limited by the description above. The constituent elements illustrated in the above-described respective embodiments can be suitably combined. Additions, omissions, substitutions, and other modifications of components can be made without departing from the concept of the invention.

For example, in the above embodiment, the example that performs the method for dissecting a submucosal layer changing each treatment instrument for the treatment instrument insertion channel 13 of the endoscope 10. Instead of this, it is possible not to change the treatment instrument or reduce the number of replacing times by using endoscope having two or more treatment instrument insertion channels. The performance of the method for dissecting a submucosal layer is more efficient because of not changing the treatment instrument or reducing the number of replacing times.

For example, in the above embodiment, although the example in which the lifting step includes the first engaging step and the second engaging step, the engaging step may be performed three times or more. The number of the engaging steps can be increased in accordance with the position or the condition of the lesion T because the plurality of barbs 43 are arranged along the longitudinal of the suture thread 40 between the first end 41 and the second end 42 all over. By increasing the engaging step, the needle 44 or the suture thread 40 is pulled in more stages and the amount of the lift of the area including the lesion T can be adjusted in more stages.

What is claimed is:

1. A method for treating a target tissue in a gastrointestinal tract in a state where a traction is applied to the target tissue by a suture thread that includes a plurality of barbs and is connected to an anchor and a needle, the method comprising;
    piercing a first area and a second area in the gastrointestinal tract with the needle such that the suture thread extends through the first area and the second area, and pulling the suture thread by grasping the needle or the suture thread after piercing the second area such that:
        the anchor is installed to the first area, and
        a first barb of the plurality of barbs engages the second area, the first area including a lesion, and the second area being different from the first area;
    releasing the grasping of the needle or the suture thread in a state where the first barb engages the second area;
    incising the first area in a state where neither the needle nor the suture thread is grasped;
    grasping the needle or the suture thread after incising the first area; and
    pulling the suture thread in a state where the needle or the suture thread is grasped such that a second barb of the plurality of barbs engages the second area, the second barb being arranged closer to the anchor than the first barb.

2. The method according to claim 1, wherein:
    an endoscope is inserted into the gastrointestinal tract,
    the first area is incised in a state of observing the first area using the endoscope,
    the endoscope is manipulated and a field of view of the endoscope is moved from the first area to the second area after incising the first area,
    the needle or the suture thread is grasped in a state of observing the second area using the endoscope, and
    the second barb engages the second area by pulling the suture thread in a state where the needle or the suture thread is grasped.

3. The method according to claim 2, wherein:
    the endoscope includes a treatment tool insertion channel that is capable of receiving forceps,
    the needle or the suture thread is grasped by the forceps inserted into the treatment tool insertion channel to pull the suture thread after piercing the second area such that:
        the anchor is installed to the first area, and
        the first barb of the plurality of barbs engages the second area, and
    the second barb engages the second area by pulling the suture thread in a state where the needle or the suture thread is grasped by the forceps after incising the first area.

4. The method according to claim 1, further comprising:
    separating the first area from a wall of the gastrointestinal tract,
    cutting the suture thread between the first area and the second area after the second barb engages the second area, and
    discharging the separated first area and a first portion of the suture thread including the anchor to an outside of the gastrointestinal tract after cutting the suture thread between the first area and the second area.

5. The method according to claim 4, further comprising:
    separating the needle and a second portion of the suture thread that is different from the first portion from the second area after cutting the suture thread between the first area and the second area; and
    suturing an incised portion of the gastrointestinal tract using the second portion of the suture thread and the needle, the incised portion being created by the incising and the separating of the first area from the wall of the gastrointestinal tract.

6. The method according to claim 1, wherein the needle has a piercing distal end configured to pierce tissue and a proximal end, wherein the proximal end is connected to a distal end of the suture thread.

7. The method according to claim 1, wherein the second area is disposed at a position facing the first area.

8. The method according to claim 1, wherein at least part of the first area is lifted when the suture thread is pulled after piercing the second area, and the at least part of the first area is held in a lifted state by the first barb engaging the second area after the grasping of the needle or the suture thread is released.

9. The method according to claim 8, wherein the first area is in the lifted state during the incising of the first area in the state where the neither the needle nor the suture thread is grasped.

10. The method according to claim 8, wherein when the at least part of the first area is lifted, the amount of pull is varied by adjusting an amount of air supply into the gastrointestinal tract.

* * * * *